(12) United States Patent
Yu et al.

(10) Patent No.: US 7,888,109 B2
(45) Date of Patent: Feb. 15, 2011

(54) APPARATUS AND METHODS FOR DETECTING NUCLEIC ACID IN BIOLOGICAL SAMPLES

(75) Inventors: Cheung Hoi Yu, Hong Kong (HK); Lok Ting Lau, Kowloon (HK); Ka Wai Wong, New Territories (HK)

(73) Assignee: Hai Kang Life Corporation Limited, Shau Kei Wan (HK)

( * ) Notice: Subject to any disclaimer, the term of this patent is extended or adjusted under 35 U.S.C. 154(b) by 155 days.

(21) Appl. No.: 12/113,392

(22) Filed: May 1, 2008

(65) Prior Publication Data

US 2008/0242562 A1 Oct. 2, 2008

Related U.S. Application Data

(62) Division of application No. 10/686,252, filed on Oct. 16, 2003, now Pat. No. 7,390,622.

(51) Int. Cl.
*C12M 1/00* (2006.01)
(52) U.S. Cl. .................................................. 435/288.1
(58) Field of Classification Search .................. None
See application file for complete search history.

(56) References Cited

U.S. PATENT DOCUMENTS

| 5,605,662 | A | 2/1997 | Heller et al. |
| 6,291,166 | B1 | 9/2001 | Gerdes et al. |
| 6,306,348 | B1 | 10/2001 | Havens et al. |
| 6,716,620 | B2 | 4/2004 | Bashir et al. |
| 2001/0053535 | A1 | 12/2001 | Bashir et al. |
| 2002/0085954 | A1 | 7/2002 | Havens et al. |
| 2002/0090649 | A1 | 7/2002 | Chan et al. |
| 2002/0177135 | A1 | 11/2002 | Doung et al. |
| 2003/0036054 | A1 | 2/2003 | Ladisch et al. |
| 2003/0157587 | A1 | 8/2003 | Gomez et al. |
| 2004/0033496 | A1 | 2/2004 | Yu et al. |
| 2004/0053290 | A1 | 3/2004 | Terbrueggen et al. |

FOREIGN PATENT DOCUMENTS

| CN | 1431493 | 7/2003 |
| EP | 0 395 300 | 10/1990 |
| JP | 9/503307 | 3/1997 |
| JP | 09-503307 | 3/1997 |
| WO | WO 96/01836 | 1/1996 |
| WO | WO 96/07917 | 3/1996 |
| WO | WO 01/43870 | 6/2001 |
| WO | WO 01/79529 | 10/2001 |
| WO | WO 02/31463 | 4/2002 |
| WO | WO 02/43864 | 6/2002 |
| WO | WO 2004/015138 | 2/2004 |

OTHER PUBLICATIONS

International Search Report issued in corresponding International Application No. PCT/CN2004/001180 dated Mar. 3, 2005.
Supplementary European Search Report issued in corresponding Application No. 04789841.6-2204 dated Dec. 9, 2009.

*Primary Examiner*—Kenneth R Horlick
*Assistant Examiner*—David C Thomas
(74) *Attorney, Agent, or Firm*—Buchanan Ingersoll & Rooney PC (57) ABSTRACT

There are disclosed apparatus and methods for the field-assisted acceleration of biological processes involving charged entities, including in particular the detection of target DNA in a biological sample. A reaction cell is provided with a dielectric surface, and a field is generated by inducing charge-separation in the dielectric material by applying a potential to an electrode in contact with the dielectric material.

14 Claims, 7 Drawing Sheets

FIG.7 though ambi-US 7,888,109 B2

APPARATUS AND METHODS FOR DETECTING NUCLEIC ACID IN BIOLOGICAL SAMPLES

CROSS REFERENCE TO RELATED APPLICATIONS

This application is a divisional of U.S. application Ser. No. 10/686,252, filed Oct. 16, 2003, now U.S. Pat. No. 7,390,622 which is herein incorporated by reference in its entirety for all purposes.

FIELD OF THE INVENTION

This invention relates to apparatus and methods for detecting nucleic acid in biological samples. In particular the present invention relates to a novel apparatus and method for detecting DNA sequences using field-assisted nucleic acid hybridization and to methods for optimizing the performance of such apparatus, and further the present invention extends to the use of field-assisted hybridization in any biological process that includes charged entities.

BACKGROUND OF THE INVENTION

The emergence of high-density polynucleotide (e.g. DNA or RNA) array technology has transformed the basic concepts of genomics and proteomics analysis. The transition from "dot blots" to "arrays on glass slides" and then to DNA microarrays (also known as DNA chips) has revolutionised the industry by making large-scale clinical diagnostic testing and screening processes realistic for practical applications. As is well-known, a typical microarray, with reactive sites in a predetermined configuration on a substrate, will exhibit a binding pattern when exposed to a sample with target nucleic acid fragments having a base sequence complementary to that of the capture fragments attached on the reactive sites. The binding pattern and the binding efficiency can be detected by optical or electronic methods when an appropriate detection mechanism is used, which may include for example fluorescent labeling, current detection or impedance measurement.

The use of electrically-assisted nucleic acid hybridization is a known technique in the analysis of biological samples containing DNA, e.g. blood, plasma, urine etc. Conventionally, a chip for DNA detection is formed from one of a variety of materials including glass, silica and metal. On the surface of the chip a number of electrical contacts are formed using known techniques. To detect a particular DNA sequence in a biological sample, capture probes consisting of complementary DNA fragments are attached to the chip surface by means of an attachment layer which is conventionally an agarose gel. If a biological sample contains the target DNA, the target DNA will bind to the complementary DNA fragments by hybridization, and various imaging techniques may be used to detect such hybridization and thus the presence in the sample of the target DNA.

PRIOR ART

Nucleic acid fragments are electrically charged and thus can be attracted towards a particular site by electrostatic attraction by the use of electrodes and thus by the application of an appropriate electrical current the hybridization process may be accelerated and thus the detection process is also accelerated. However, it is not possible to use the electrode in direct contact with the nucleic acid fragments because of the danger of electrochemical degradation or electrolysis of the sample. Conventionally therefore a permeation/attachment layer is normally coated on the electrode as shown in U.S. Pat. Nos. 5,605,662 and 6,306,348. The permeation/attachment layer is normally made from porous materials, e.g. sol-gel materials, porous hydrogel materials, porous oxides and serves to allow the selective diffusion of small ions and also as an attachment surface for the capture probes. Direct contact of the nucleic acid fragments with the electrode is reduced owing to the size of the pores of the porous materials which are generally too small to allow the larger nucleic acid fragments to pass through.

When a voltage is applied to the electrode underneath the permeation/attachment layer, the devices of the prior art can provide electrophoretic transport effects without electrochemical degradation of the sample and can thus enhance hybridization. However, such prior techniques for enabling electrically-induced hybridization are not without their drawbacks. For example, porous materials such as hydrogels and polymers are vulnerable to deterioration under contact with aqueous solutions, various chemicals and a number of ambient factors. The preparation of sol-gel materials are costly and complicated, increasing the manufacturing costs. Furthermore the porous materials are naturally fragile and susceptible to adsorption and the trapping of undesired foreign materials such as moisture hydrocarbons in air, resulting in a shorter-shelf-life of the devices.

SUMMARY OF THE INVENTION

According to the present invention there is provided apparatus for detecting target nucleic acid in a sample, comprising a substrate formed with at least one reaction cell, wherein said reaction cell includes an attachment surface formed of a dielectric material for the attachment of nucleic acid capture probes, and wherein a metal electrode is provided in direct contact with said dielectric material. The sample may comprise biological substances and the sample may be wastewater, solution or reagent. The sample may also be a biological sample such as blood, plasma or urine.

Preferably the electrode is provided beneath the attachment surface, that is to say in contact with a side of the dielectric material opposite from the attachment surface. Conceivably, however, it could be applied in contact with a side of the dielectric material or even in contact with the attachment surface itself.

In preferred embodiments of the invention the dielectric material is preferably an oxide, for example it may be selected from the group consisting of $Al_2O_3$, $SiO_2$ and $Ta_2O_5$. The metal electrode for example may be formed of aluminum.

In preferred embodiments of the invention the apparatus may comprise a multilayer structure comprising a first base layer, a second insulating layer formed on said base layer, a third layer formed on said insulating layer and comprising patterned conductive regions defining at least one metal electrode, and a fourth layer comprising at least one region of dielectric material, wherein each said metal electrode in said third layer is covered by a region of dielectric material in said fourth layer. Preferably the patterned conductive regions of the third layer are separated by regions formed of dielectric material. Still more preferably the regions of dielectric material in said fourth layer are separated by regions of a passivation material, and the regions of passivation material may extend over the edges of said regions of dielectric material to define said reaction cells.

Viewed from another broad aspect the present invention provides a method of performing field-assisted hybridization in the detection of nucleic acid targets from a biological sample, comprising the steps of providing a reaction cell having an attachment surface formed of a dielectric material, providing a metal electrode beneath in direct contact with said dielectric material, attaching nucleic acid capture probes to said attachment surface, adding a sample to said reaction cell, and providing an electrical potential to said electrode. The sample may comprise biological substances and the sample may be wastewater, solution or reagent. The sample may also be a biological sample such as blood plasma or urine.

The electrical potential may be applied as a continuous potential, or may be a smoothly varying, or pulsed potential.

Viewed from another broad aspect the present invention also provides a method of attracting or repelling electrically-charged entities to or from a surface of a reaction cell when performing a biological reaction, comprising the steps of providing a dielectric material as said surface, and generating an electrical field by inducing charge-separation in said dielectric material. The electrically charged entities may be nucleic acid molecules.

Viewed from a still further aspect the invention also extends to a method of forming an array of reaction cells for performing biological analysis, comprising the steps of patterning metal electrodes on an insulating substrate, depositing regions of dielectric material on said metal electrodes, and forming a rim around the edges of upper surfaces of said regions of dielectric material so as to define said reaction cells.

Preferably, for example, the method may comprise depositing a layer of metal on an insulating surface, covering a desired pattern of said metal layer with a photoresist and removing the remainder of said metal layer by an etching process, depositing a layer of said dielectric material over said patterned metal whereby said dielectric material covers said patterned metal and occupies the areas between said patterned electrodes, depositing a passivation layer over said layer of dielectric material, pattering said passivation layer with a photoresist and removing said passivation layer to open said dielectric material where it covers said metal electrodes to define reaction said cells.

BRIEF DESCRIPTION OF THE DRAWINGS

Some embodiments of the invention will now be described by way of example and with reference to the accompanying drawings, in which:—

DETAILED DESCRIPTION OF PREFERRED EMBODIMENTS

Figure 1:
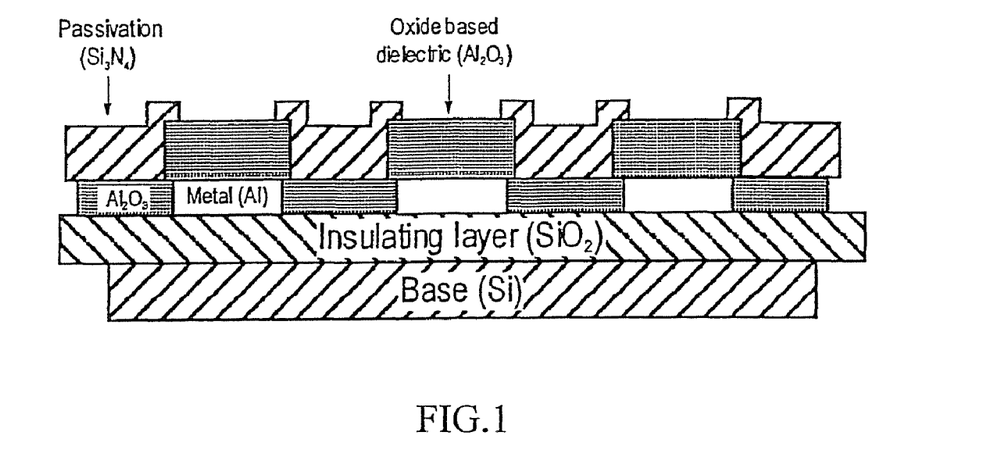
FIG. 1 is a sectional view through a chip in accordance with an embodiment of the present invention.

FIG. 1 shows in section a part of an embodiment of the present invention that includes three cells for receiving a sample-containing buffer solution, but it will be understood that any number of cells could be provided, and they would normally be formed in a rectangular array.

Figure 4:
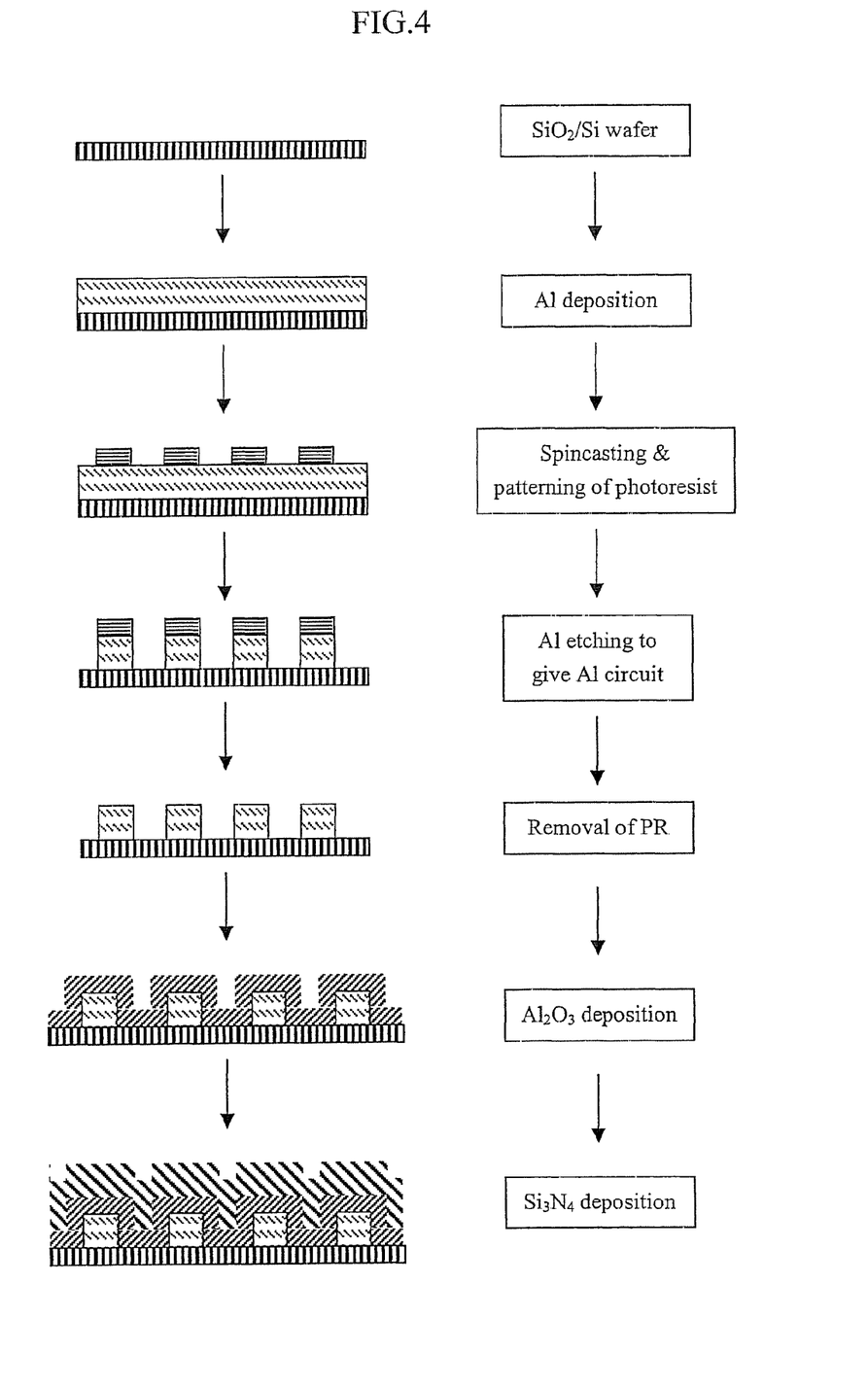
FIG. 4 illustrates the steps in a possible fabrication process, FIGS. 5(a) and (b) show first test results, FIGS. 6(a) and (b) show second test results, and FIGS. 7(a) and (b) show third test results.

The device according to an embodiment of the invention is fabricated by sequential deposition onto a silicon substrate using conventional deposition techniques. Firstly, (FIG. 4(a)) an insulating layer formed of $SiO_2$ of a thickness of between about 200 nm to 500 nm is formed on the Si substrate by any suitable technique including thermal oxidation or by any suitable deposition technique such as for example sputtering, electron beam evaporation and the like. On top of the insulating layer is formed (FIG. 4(b)) a layer of aluminum of a thickness of between about 500 nm to 1000 nm again using any conventional deposition techniques.

Once the layer of aluminum has been formed, it is patterned (FIG. 4(c)) using a layer of photoresist and the unmasked areas are removed by etching (FIG. 4(d)) and the photoresist is removed (FIG. 4(e)). The chip is then coated (FIG. 4(f)) with $Al_2O_3$ to a thickness of between 50-500 nm with regions of $Al_2O_3$ being formed between the aluminum regions that are formed on the silicon dioxide substrate. A passivation layer of (for example) $Si_3N_4$ is then deposited (FIG. 4(g)) on the $Al_2O_3$ by means of plasma enhanced chemical vapor deposition or similar techniques. The passivation layer is then patterned with a photoresist (FIG. 4(h)) and the passivation layer is then etched (FIG. 4(i)) to open up the $Al_2O_3$ areas that are to become the attachment surfaces of the reaction cell. Finally the photoresist is removed (FIG. 4(j)).

The result of this fabrication process is the multi-layer structure of FIG. 1. Regions of aluminum are formed on the insulating layer of silicon dioxide and these aluminum regions are separated by $Al_2O_3$. Formed on top of the layer of aluminum and $Al_2O_3$ is a layer that comprises regions of $Al_2O_3$ located above the regions of aluminum and separated from each other by the passivation material $Si_3N_4$ which covers the $Al_2O_3$ regions separating the aluminum regions on the lower later. The passivation material also extends to cover the edges of the top $Al_2O_3$ so as to define a surface for a biological sample to be placed for analysis.

It will thus be understood that in the example shown in FIG. 1 the chip is formed with three cells 1-3 each formed of $Al_2O_3$ with an underlying pad of aluminum. Although not shown in FIG. 1 when the aluminum regions are formed by etching, electrical connections may also be formed that allow an electrical potential to be applied to the aluminum regions.

Figure 2:
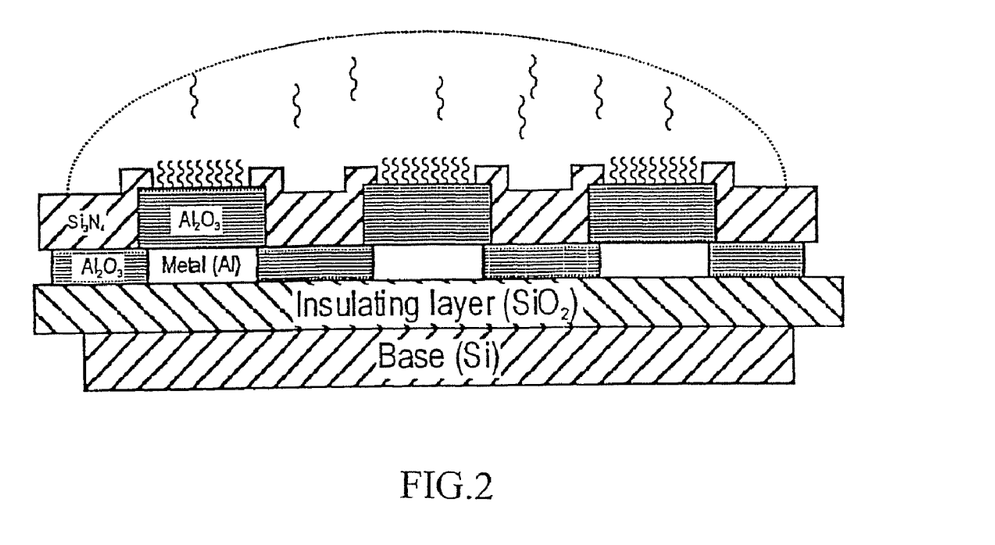
FIG. 2 is a view similar to FIG. 1 but showing the chip in use.

Once the chip of FIG. 1 has been fabricated it can be used as the basis for a number of different biological tests and assays. In particular each cell 1-3 in FIG. 1 may be provided with suitable capture probes as shown in FIG. 2. Depending on the tests to be performed, each cell may be provided with the same capture probes or with different capture probes, the capture probes having nuclei acid fragments that are complementary to fragments in the sample that the test or assay is looking for. In the example of FIG. 2, the cells 1-3 are all identical and a drop of sample containing buffer solution is added to the cell so that it covers all three cells.

As will be understood by those skilled in the art, if the sample contains fragments of nucleic acid that are complementary to the capture probes, they will bind to the capture probes by the process of hybridization and this may be detected by known techniques. Since the nucleic acid fragments are electrically charged, this hybridization can be enhanced by providing an electrical field that will attract desired nucleic acid fragments towards the attachment surface and the capture probes. The mechanism by which this may be done is shown in FIG. 3.

Figure 3:
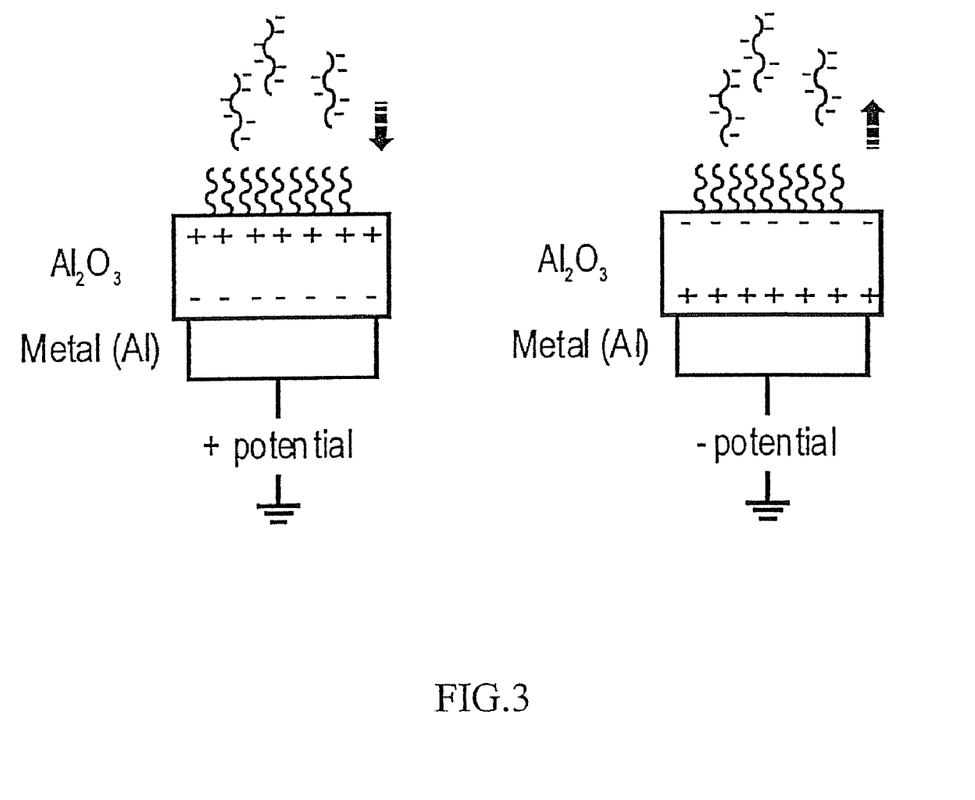
FIG. 3 is a schematic illustration showing the underlying principle of preferred embodiments of the present invention.

In particular, as shown in FIG. 3, if a potential is applied to the aluminum electrode underlying a cell, then because $Al_2O_3$ is a dielectric material charge separation will occur within the $Al_2O_3$ the polarity of which will depend on the polarity of the voltage applied to the aluminum electrode beneath the $Al_2O_3$. As shown on the left of FIG. 3, if a positive potential is applied to the aluminum electrode, then the upper surface of the $Al_2O_3$ will also have a positive potential which would attract negatively charged fragments, and repel positively charged fragments. Conversely, if a negative potential is applied to the aluminum electrode, then the upper surface of the $Al_2O_3$ will also have a negative potential which would attract positively charged fragments, and repel negatively charged fragments as shown in the right-hand side of FIG. 3. Thus selectively applying an electrical potential to the aluminum electrodes that are directly underneath and in direct contact with the $Al_2O_3$ attachment surface enables the selective attraction/repelling of nucleic acid fragments and thus enables electrically-induced hybridization. It should be understood that the potential can be applied in many different ways. The potential could for example be a constant continuous potential, may be smoothly varying, or may be pulsed either with regular pulses or in any desired pattern.

A particular advantage of the present invention, at least in its preferred forms, in contrast with the prior art is that undesired electrochemical reactions and/or electrolysis can be completely avoided since there is no electron transfer between the sample solution and the surface of the dielectric layer. The nucleic acid fragments can thus be electrically drawn to the attachment surface without electrochemical degradation. A further important advantage of the field-assisted hybridization method and apparatus of the present invention, at least in preferred forms, is that the salt concentration and pH value of the sample will not be changed. These parameters are crucial factors influencing the hybridization efficiency and the stability of the hybridized nucleic acid fragments. Prior art electrically-assisted hybridization techniques lead to significant changes in the salt concentration and the pH due to electrochemical reactions and other techniques, such as special buffer solutions, are required in order to compensate for these effects. A further advantage of the present invention is that no electrochemical reactions will occur and in turn this will mean that the solutions/reagents involved in the detection process will not be disturbed. There will be no bubble formation and/or precipitation during the detection process, which is important in improving the quality of the detected signal.

It should also be understood that while preferred embodiments of the present invention are described in the context of accelerated hybridization in the detection of nucleic acid fragments, the invention is more generally applicable to any biological process that involves electrically-charged entities and where it is desired to be able to control the movement of such electrically-charged entities by attracting or repelling such entities to or from a surface.

Figure 5:
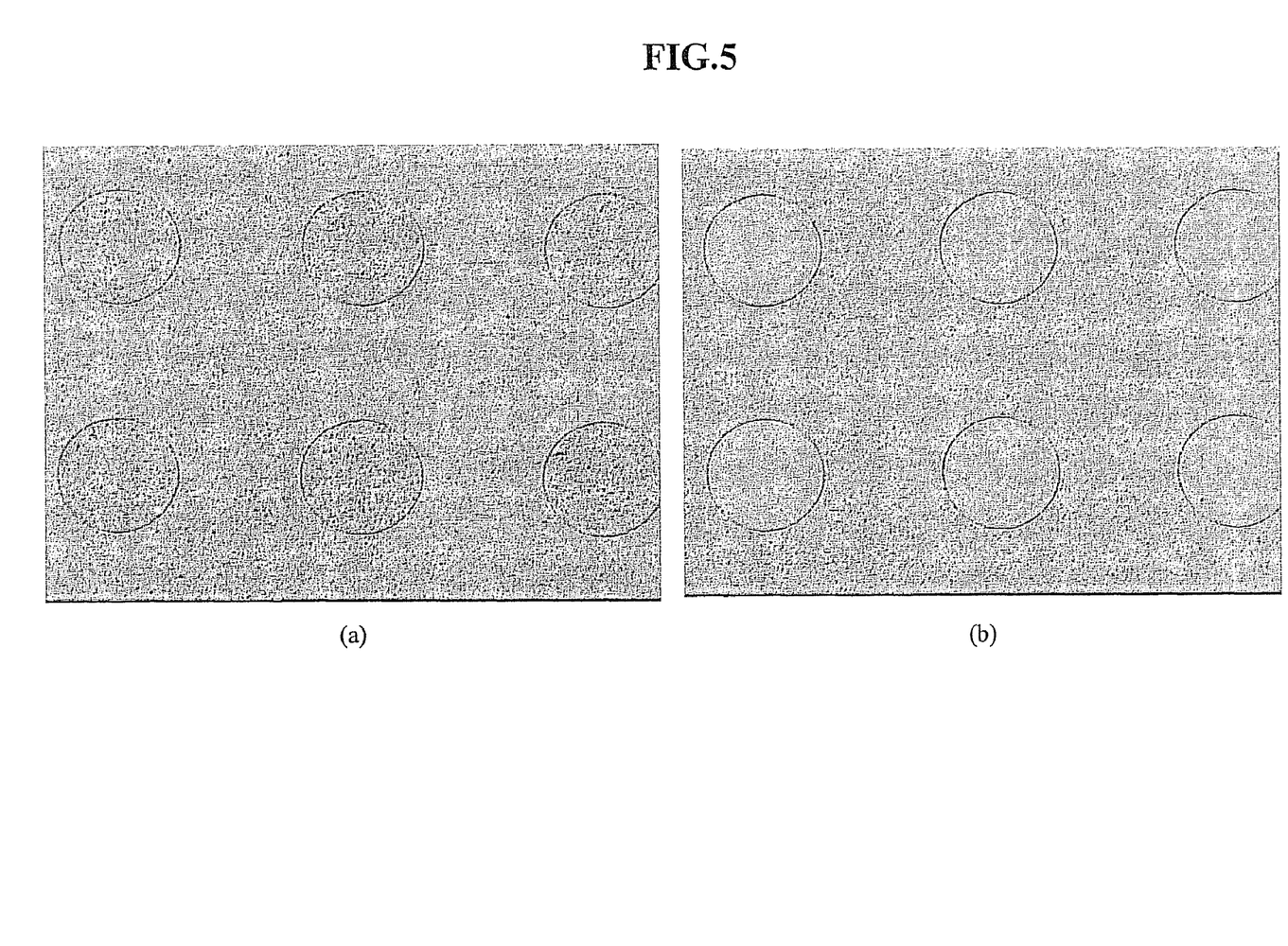
Figure 6:
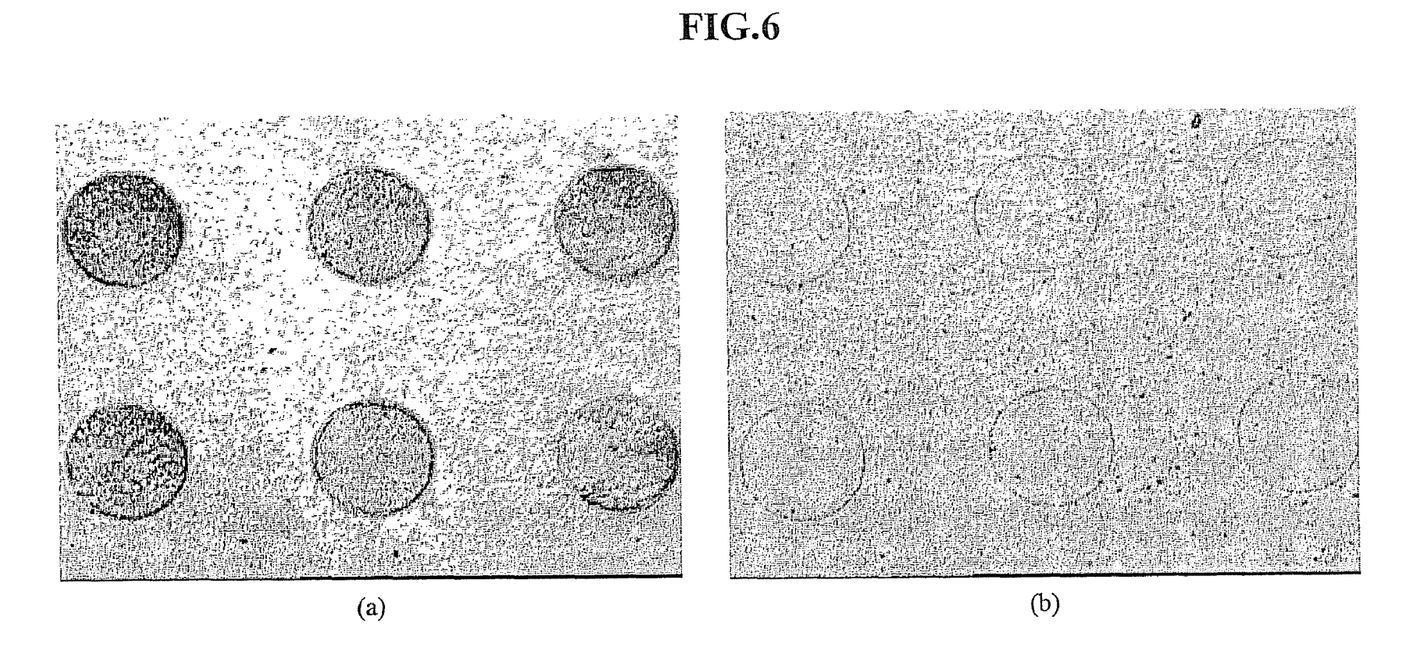
Figure 7:
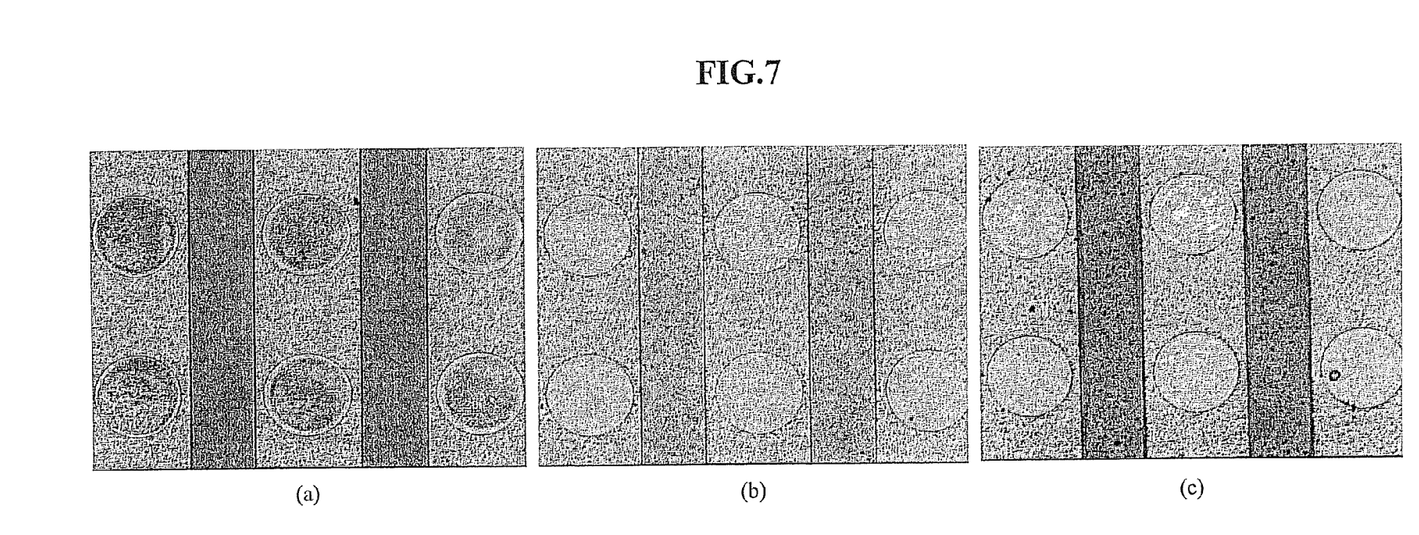

FIGS. 5 to 7 show a number of experimental results using the structure of FIGS. 1 to 3 with and without an electrical potential applied to the aluminum electrodes beneath the cells. It will of course be understood that in all of these examples the reaction times, applied voltages and other parameters are purely exemplary and may be varied as desired.

FIGS. 5(a) and (b) show a control in which in neither case is an electrical potential applied to the aluminum electrodes and therefore the hybridization proceeds without electrical assistance. In this Example the target oligomers in the sample are synthetic β-actin (91 bases, pure) and the hybridization time is 90 minutes. The target oligomers are present in the sample of FIG. 5(a) and not present in the sample of FIG. 5(b). In neither FIG. 5(a) or 5(b) is an electrical potential applied to the aluminum electrode, but the cells are clearly darker in FIG. 5(a) than 5(b) owing to the presence of the target oligomers in the sample of FIG. 5(a).

In FIGS. 6(a) and (b) the conditions are the same as in FIGS. 5(a) and (b) in that the same target oligomers are provided in the sample of FIG. 6(a) and no target oligomers are provided in the sample of FIG. 6(b). In this example, however, a potential of +10V is applied to the aluminum electrodes and the hybridization time is reduced to 10 minutes. A comparison of FIGS. 5(a) and 6(a) shows that in FIG. 6(a) the cells are much darker clearly illustrating even though the hybridization time has been substantially reduced, demonstrating the effectiveness of the applied voltage in accelerating the hybridization. The similarity between FIGS. 5(b) and 6(b) where no target oligomers are present shows that the applied voltage does not lead to any false positive results.

FIG. 7(a)-(c) illustrate a third example in which the target oligomers in the sample are avarian influenza virus (AIV) H5 subtype (250 bases mixed with other non-specific oligomers). In all three cases (a)-(c) the hybridization time is 10 minutes. The differences between FIGS. 7(a)-(c) are as follows: In FIG. 7(a) target oligomers are present in the sample and an electrical potential of +10V is applied to the aluminum electrodes beneath the cells; In FIG. 7(b) no target oligomers are present in the sample and an electrical potential of +10V is applied to the aluminum electrodes beneath the cells; and in FIG. 7(c) target oligomers are present in the sample but no electrical potential is applied to the aluminum electrodes beneath the cells. Again this example shows that with a hybridization time of only 10 minutes, the application of a +10V potential to the electrode results in accelerated hybridization and strong signal (very dark areas in the cells of FIG. 7(a)). In comparison the similarity in appearance between FIG. 7(b) (without target and with applied potential) and FIG. 7(c) (with target but without applied potential) shows that it is not possible to obtain effective hybridization in the same time period (10 minutes) without electrically assisted hybridization.

The present invention at least in its applied forms provides a simple low-cost device that allows nucleic acid field-assisted hybridization and/or other biological processes to proceed at a much faster rate with high performance that can be applied to a large number of possible applications. The present invention employs the principle of charge-separation in a dielectric material that is in contact with an electrode to which a potential is applied. In the embodiments described above the electrode is aluminum and the dielectric material is $Al_2O_3$, but other combinations of metal electrode and dielectric attachment surface are also possible. For example, $SiO_2$, $Ta_2O_5$ may be used as oxide based dielectric materials for the attachment surface.

In contrast with the prior art devices that use a permeation layer, the oxide based dielectric layer in direct contact with the electrode provides a structure that is robust, compact, chemically inert towards most of the acids, alkalis and other reagents commonly used in biological reactions. The structure is also stable with regards to ambient factors such as temperature and humidity and is less vulnerable to physical damage. The production costs are lower and the device can be manufactured very easily using standard deposition techniques and other microelectronics fabrication techniques. Indeed the use of such microelectronics deposition and fabrication techniques in the manufacture of the devices of the present invention also has the advantage that the devices can readily be incorporated into other devices made using the same or similar technology.

The invention claimed is:

1. Apparatus for detecting target nucleic acid in a sample, comprising a substrate formed with at least one reaction cell, wherein said reaction cell comprises a dielectric attachment layer formed of a dielectric material defining an attachment surface for the attachment of nucleic acid capture probes, and wherein a metal electrode is provided in direct contact with said dielectric attachment layer, wherein said dielectric attachment layer is over 50 nm thick such that applying an electrical potential to said metal electrode causes a charge separation in said dielectric attachment layer without generating a flow of electric current or causing transfer of electrons between said layer and a sample in said reaction cell.

2. Apparatus as claimed in claim 1 wherein said electrode is in contact with a side of said dielectric material opposite from said attachment surface.

3. Apparatus as claimed in claim 1 wherein said dielectric material is an oxide.

4. Apparatus as claimed in claim 3 wherein said dielectric material is selected from the group consisting of $Al_2O_3$, $SiO_2$ and $Ta_2O_5$.

5. Apparatus as claimed in claim 1 wherein said electrode is formed of aluminum.

6. Apparatus as claimed in claim 1 wherein said dielectric material comprises $Al_2O_3$ and said electrode is formed of aluminum.

7. Apparatus as claimed in claim 1 comprising a multilayer structure comprising a first base layer, a second insulating layer formed on said base layer, a third layer formed on said insulating layer and comprising patterned conductive regions defining at least one metal electrode, and a fourth layer comprising at least one region of dielectric material, wherein each said metal electrode in said third layer is covered by a region of dielectric material in said fourth layer.

8. Apparatus as claimed in claim 7 wherein the patterned conductive regions of said third layer are separated by regions formed of dielectric material.

9. Apparatus as claimed in claim 7 wherein said regions of dielectric material in said fourth layer are separated by regions of a passivation material.

10. Apparatus as claimed in claim 9 wherein said regions of passivation material extend over the edges of said regions of dielectric material to define said reaction cells.

11. Apparatus as claimed in claim 1 wherein said sample comprises biological substances.

12. Apparatus for detecting target biological material in a sample, comprising a substrate formed with at least one reaction cell, wherein said reaction cell comprises a surface formed of a dielectric material, wherein a metal electrode is provided in direct contact with said dielectric material, and wherein said dielectric material is over 50 nm thick such that applying an electrical potential to said metal electrode can cause a charge separation in said dielectric material without generating a flow of electric current or causing transfer of electrons between said electrode and a sample in contact with said dielectric material.

13. A method of forming an array of reaction cells for performing biological analysis, comprising the steps of patterning metal electrodes on an insulating substrate, depositing regions of dielectric material on said metal electrodes, and forming a rim around the edges of upper surfaces of said regions of dielectric material so as to define said reaction cells, wherein said dielectric material is over 50 nm thick such that applying an electrical potential to said metal electrodes can cause a charge separation in said dielectric material without generating a flow of electric current or causing transfer of electrons between said electrodes and a sample in said reaction cells.

14. A method as claimed in claim 13 comprising depositing a layer of metal on an insulating surface, covering a desired pattern of said metal layer with a photoresist and removing the remainder of said metal layer by an etching process, depositing a layer of said dielectric material over said patterned metal whereby said dielectric material covers said patterned metal and occupies the areas between said patterned electrodes, depositing a passivation layer over said layer of dielectric material, patterning said passivation layer with a photoresist and removing said passivation layer to open said dielectric material where it covers said metal electrodes to define reaction said cells.

* * * * *